Figure 1:
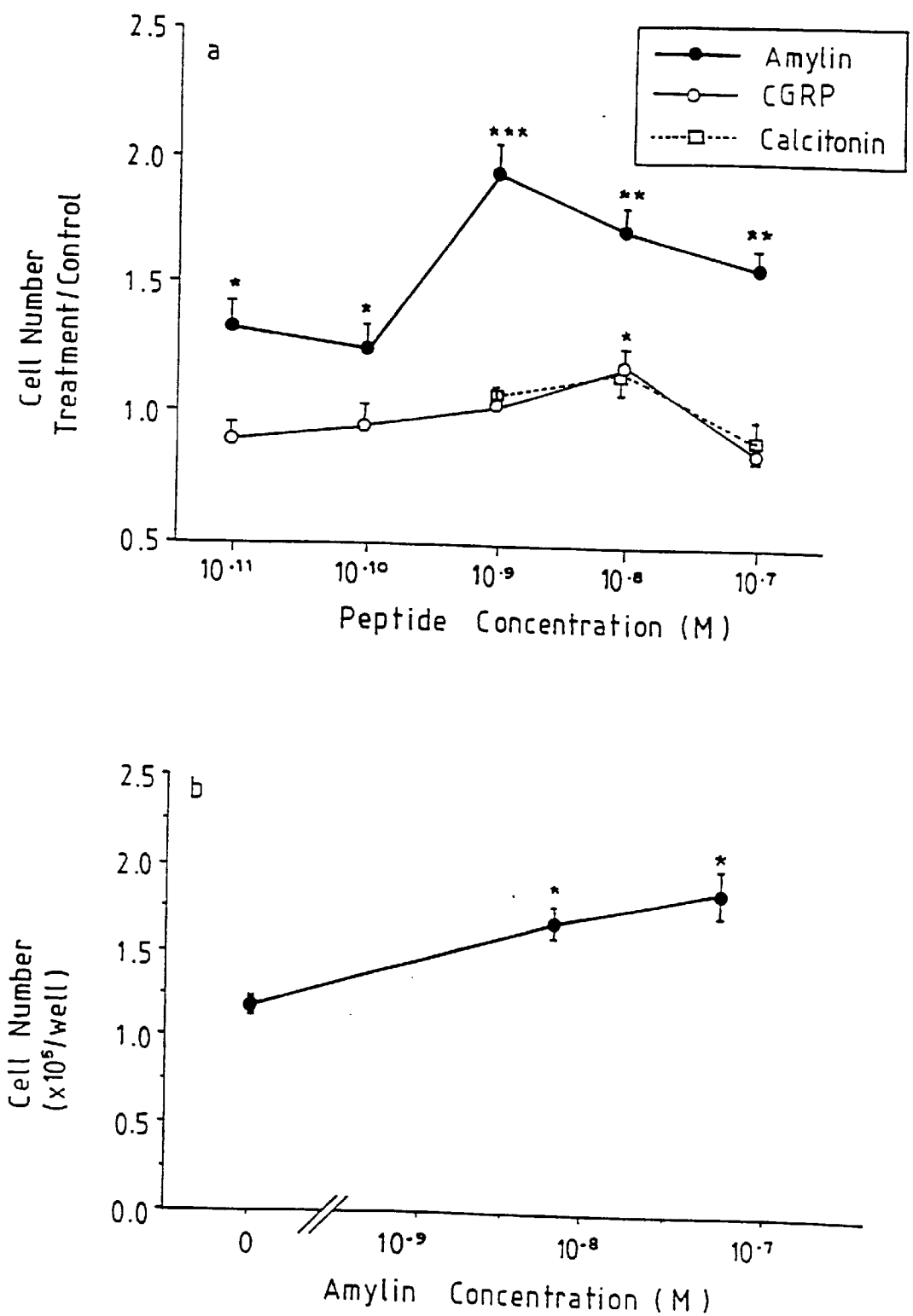

United States Patent [19]
Reid et al.

[11] Patent Number: 5,922,677
[45] Date of Patent: Jul. 13, 1999

[54] THERAPEUTIC METHOD AND COMPOUNDS OF USE THEREIN

[75] Inventors: Ian Reginald Reid; Jillian Cornish, both of Auckland, New Zealand

[73] Assignee: Auckland UniServices Limited, Auckland, New Zealand

[21] Appl. No.: 08/765,542

[22] PCT Filed: Jul. 12, 1995

[86] PCT No.: PCT/NZ95/00062

§ 371 Date: Jan. 8, 1997

§ 102(e) Date: Jan. 8, 1997

[87] PCT Pub. No.: WO96/02269

PCT Pub. Date: Feb. 1, 1996

[30] Foreign Application Priority Data

Jul. 13, 1994 [NZ] New Zealand .............................. 260995
Jul. 13, 1994 [NZ] New Zealand .............................. 260996

[51] Int. Cl.$^6$ .......................... A61K 37/00; A61K 37/02; C07K 14/435
[52] U.S. Cl. ............................ 514/12; 530/324; 530/300
[58] Field of Search .................... 530/324, 300; 514/2, 12

[56] References Cited

U.S. PATENT DOCUMENTS 5,124,314  6/1992  Cooper ........................................ 514/4
5,298,605  3/1994  Westermark et al. ................. 530/387.9
5,405,831  4/1995  MacIntyre .................................. 514/4

FOREIGN PATENT DOCUMENTS

B-21575/88  7/1989  Australia .

OTHER PUBLICATIONS

Ried et al. Parathyroid hormone depresses cytosolic pH and DNA synthesis in osteoblast–like cells © 1988, Am. J. Physiol. 255:E9–E15.
Calcif. Tissue Int. vol. 56, pp. 54–61 (1995). D. F. Romero et al., "Amylin Increases Bone Volume but Cannot Amelionate Diabetic Ostoperia". See in particular Abstract and p. 57.
Biochem. Biophys. Res. Comm., vol. 207, No. 1, pp. 133–139, Cornish, J. et al., "Amylin Stimulates Osteoblast Proliferation and Increases Mineralized Bone Volume in Adult Mice", Feb. 6, 1995. See in particular Abstract, pp. 134, 136 and 137.
WO 88/02863 A (University of Minnesota), Apr. 21, 1988. See "Experimental Portion A", pp. 9 and 10.
Endocrine Reviews, vol. 15, No. 2, pp. 163–201 (1994) Cooper, G.J.S. "Amylin Compared with Calcitonin Gene–Related Peptide: Structure, Biology, and Relevance to Metabolic Disease". See p. 186.
Bone, vol. 14, pp. 167–172 (1993), Pietschmann, P. et al., Inhibitory Effect of Amylin on Basal and Parathyroid Hormone–Stimulated Bone Resorption in Cultured Neonatal MouseCalvaria.
Trends in Endocrinology and Metabolism, vol. 4, No. 8, pp. 255–259 (1993). Mone Zaidi et al. "Amylin in Bone Conservation: Current Evidence and Hypothetical Considerations".
J. Cellular Physiology vol. 153, pp. 6–14 (1992) Tamura, T., et al "Mechanism of Action of Amylin in Bone". See Abstract, pp. 7,9 to 13 in particular.
Biochem. Biophys. Res. Comm. vol. 162, No. 2, pp. 876–881 (1989). Datta, H.K. et al "In vivo and In Vitro effects of amylin and amylin–amide on calcium metabolism in the rat and rabbit".
Proc. Nat. Acad. Sci. USA, vol. 184, pp. 8628–8632 (1978) Cooper, G.J.S. et al "Purification and characterisation of a peptide from amyloid–rich pancreases of Type 2 diabetic patients".
Experimental Physiology, vol. 78, pp. 183–196 (1993). A.S.M. Towdihul Alam et al "Amylin Inhibits Bone Resorption by a Direct Effect on the Motility of Rat Osteoclasts". See in particular p. 195.
J. Bone Miner. Research vol. 15, S229, Abstract 621 (1990) Datta, H.K. et al Amylin–amide competes with CGRP bindin sites on osteoblast–like osteosarcoma cells.
J. Bone Miner. Research vol. 7, No. 9, pp. 1113–1116 (1992) Wimala Wansa, S.J. et al "Hypocalcemic Actions of Amylin Amide in Humans". See in particular p. 1114.
Datta et al 1990 Biochem. Soc. Trans. 18:1276.
Tamura et al 1992 Calif. Tissue Int. 50(Suppl 1):A42.

*Primary Examiner*—Karen Cochran Carlson
*Attorney, Agent, or Firm*—Fish & Richardson P.C.

[57] ABSTRACT

The use of amylin as an agent for stimulation of bone growth is provided together with methods of stimulating bone growth comprising subjecting bone to an effective amount of amylin or amylin agonists. Medicaments containing amylin or an amylin agonist are provided. The amylin or amylin agonist is preferably in the form in which the presence of TFA is minimized or totally removed. Preferably a salt with an inert anion is used. The method will be particularly useful in treating bone disorders where stimulation of bone growth is required. The treatment of osteoporosis, bone loss of malignancy, or endocrine disorders or arthritides or immobility and disuse and in fractures are examples of the many disorders which may be treated. Previous bone loss can be reversed, and bone density can be increased or maintained.

11 Claims, 3 Drawing Sheets

THERAPEUTIC METHOD AND COMPOUNDS OF USE THEREIN

TECHNICAL FIELD

This invention relates to the use of amylin as an agent for stimulation of bone growth and hence its use in the treatment of bone disorders where stimulation of bone growth is required and novel compounds for use therein.

BACKGROUND OF INVENTION

Amylin is a 37-amino acid peptide cosecreted with insulin from the beta cells of the pancreatic islets. It was first reported by Cooper et al in Proceedings of the National Academy of Sciences USA 84, 8628 (1987) and is the subject of European Patent 289287. Amylin has the following peptide sequence:

```
Lys-Cys-Ans-Thr-Ala-Thr-Cys-Ala-Thr-Gln-
1               5                    10

Arg-Leu-Ala-Asn-Phe-Leu-Val-His-Ser-Ser-
11              15                   20

Asn-Asn-Phe-Gly-Ala-Ile-Leu-Ser-Ser-Thr-
21              25                   20

Asn-Val-Gly-Ser-Asn-Thr-Tyr
31              35
```

The native molecule contains a disulfide bridge between the cysteine residues shown at positions 2 and 7 in the primary structure, is amidated at the 3'-end, and is formed as a propeptide.

European Patent 289287 reports a number of novel biological effects including enhancement of hepatic glucose output, increased production of lactate from skeletal muscle and reduced action of insulin in skeletal muscle.

Amylin is also reported in European Patent 408284 as having value for treatment of bone disorders and calcium imbalance. The patent specification attributes the activity of amylin to an inhibition of osteoclast motility.

DISCLOSURE OF THE INVENTION

We have now found that administration of amylin stimulates bone growth. We believe this is the first report of the use of amylin causing measurable bone formation through increased proliferation of osteoblasts.

By the terms amylin or amylin agonist as used herein we mean amylin or any functionally effective derivative or fragment thereof or related peptide which binds to the amylin receptor and lead to amylin like effects. Fragments are described for example in EP 289287 which is herein incorporated by reference.

The invention therefore provides a method of stimulating bone growth comprising subjecting bone to the effect of an effective amount of amylin or an amylin agonist.

The invention further provides a method of stimulating bone growth through increasing osteoblast proliferation comprising subjecting the bone to the effect of an effective amount of amylin or an amylin agonist.

The method of the invention will be particularly useful for treatment of osteoporosis, bone loss of malignancy, or endocrine disorders or arthritides or immobility and disuse and in fractures by enabling the patient to reverse previous bone loss. The method can be used for treatment of bone disorders in all animals, e.g. mammals particularly humans, cattle, horses, dogs and cats.

The invention also provides a method of prophylactically increasing or maintaining bone density in a subject having a substantially normal bone density comprising the step of administering an effective amount of amylin or an amylin agonist.

By this aspect of the invention it is envisaged that patients at risk of bone deterioration will be given a regular dose of amylin or an amylin agonist to prevent likely bone deterioration. Patients at most risk are post menopausal women usually at age above 50 and men beyond 60. By "normal bone density" is meant within two standard deviations of the mean value for race, age and sex.

Administration within the scope of the invention can also be after bone density has deteriorated beyond the normal level. In view of the previously noted effect of inhibiting osteoclast activity and the effect noted by us of stimulating bone growth, treatment with amylin or an amylin agonist is capable of reversing bone loss.

Treatment of mammals can be with the homologous or heterologous amylin. Suitable amylin or amylin agonists can be those derived from animals, e.g. humans and other mammals e.g. rat, monkey, dog, cat, mouse, guinea pig, hamster, degus, rabbit, hare. The structure of these various peptides is reported in Endocrine Reviews 1994, 15 (2) 163 by Garth J S Cooper which is herein incorporated by reference.

Amylin and amylin agonists can be produced by methods well known in the art, e.g. as set forth in European Patent 289287, 309100 and 408284. Pure amylin is isolated by HPLC by these methods in the form of the trifluoroacetic acid salt (TFA salt) generally as the tetra-TFA salt.

The invention further provides for using amylin or an amylin agonist in a form in which the presence of TFA is minimised or preferably substantially totally removed. Thus amylin or the amylin agonist can be in the form of a non-TFA salt more preferably a salt with an inert anion, e.g. the hydrochloride, glucuronate, α-ketoglutarate, citrate, isocitrate, oxaloacetate, succinate, fumarate, malate, pyruvate or lactate.

These salts can be prepared in any known manner. For example, by simple reaction with the preferred acid e.g., hydrochloric acid and then freeze drying. For example the salts for use in this invention can also be made by a method involving ion-exchange. This method may be carried out in either batch or column format. Reversed-phase chromatography will generally be the most effective and therefore the most useful. Other applicable forms of chromatography which can be used include size exclusion, ion-exchange, affinity and hydrophobic interaction.

A preparation of human amylin as the trifluoroacetate salt is dissolved in a solvent such as purified water, for example purified by double distillation or reverse osmosis coupled with filtration and ion exchange or another equivalent method or another suitable solvent, to which is added either a free acid, or a salt thereof, particularly one which is soluble in the solvent. If necessary, the solution is buffered so that the pH lies between the range of 3.0 and 10.0, although preferably this will lie between 4.5 and 7.5. Buffering may be achieved either by the addition to the aqueous solution of a base such as sodium hydroxide, potassium hydroxide or ammonium hydroxide alone, in which case reliance is placed upon the anion itself to act as the buffering a gent, or through the addition of well known buffers, including for example any of those described by Dawson R M C, Elliott D C, Elliott W H, Jones K M, in Data for Biological Research, Chapter 18, 3rd Edition, Oxford Science Publications, Oxford, 1986, pp 417–452. The final concentration of the free acid or acid anion may lie between 0.001% and 10% (wt/vol), preferably between 0.1 and 1.0 (wt/vol). The mixture is then stirred (for example using a magnetic stirrer) at a fixed temperature, preferably between 0° C. and 37° C., for a suitable length of time which can be between 1 min and several days.

Acids or salts thereof which can be used in this process preferably include compatible inorganic acids such as hydrochloric and organic acids (or salts thereof) more preferably those occurring in living organisms, including but not limited to oxalic acid, glucuronic acid, pyruvic acid, lactic acid, citric acid, isocitric acid, α-ketoglutaric acid, succinic acid, malic acid, and oxaloacetic acid. In the preferred case of an aqueous solution, the desired anion can be added either as the free acid, or as a salt, preferably one which is highly soluble in water, for example the sodium or potassium salts, but also the lithium, magnesium, calcium or ammonium salts. Moreover, these salts can be used either in anhydrous or hydrated forms for example, citric acid can be used as the anhydrous free acid, the monohydrate free acid, the anhydrous trisodium salt, or the dihydrate trisodium salt.

The aqueous solution of amylin containing the appropriate anion is then applied to a reverse phase resin, which can be contained in an open vessel or a column for example a SepPak column or a chromatography column. Reversed-phase resins suitable for this purpose include but are not limited to the following: (i) silica-based C1, C3, C4, C6, C8, C18, phenyl, and cyano forms, and non-silica-based forms including polyether- and polystyrene-based e.g. as described by Carron P H, Reversed-phase chromatography of proteins, in Oliver R W A (Ed) "HPLC of macromolecules: a practical approach", IRL Press, Oxford, 1989, pp 138–139. The reversed-phase resin is then washed with appropriate volumes, which may be between one and one hundred or more volumes equivalent of the resin, with a solution of the desired anion, either in the same form as that in which the amylin preparation was dissolved, or any other suitable form. The amylin is then eluted by application of a solution of the anion in an aqueous solution of an organic solvent. Solvents which can be used for this purpose preferably include, but are not limited to acetonitrile, methanol, ethanol, propan-1-ol, propan-2-ol, butan-1-ol, and 2-methoxyethanol or mixtures thereof. The proportion of organic solvent in the aqueous phase can be fixed, for example, acetonitrile:water (70:30 (vol/vol)). Alternatively the solvent can be applied in the form of linear or stepped gradient, for example, elution can be performed by a solution of a solvent which varies in proportion between 0 and 100% (vol/vol) of the aqueous phase, such as an acetonitrile solution in water which varies between 0% and 100% (vol/vol). A preferred scheme for the elution of amylin salts other than trifluoroacetate salts from a reversed phase column is given in a modification of the method described by Cooper G J S, Willis A C, Clark A, Turner R C, Sim R B, Reid K B M, "Purification and characterization of a peptide from amyloid-rich pancreases of type II diabetic patients", Proc Natl Acad Sci USA 1987; 84:8628–8632. The difference from that method being that trifluoracetic acid in the example is replaced by a salt with chosen anion or free acid.

Once the amylin is eluted from the reversed phase resin in this manner, it may be further purified, for example by dialysis. The chosen pure amylin salt is then obtained by removal of the solvent, for example by rotary distillation or by centrifugation under vacuum.

For use in therapy, amylin can be utilised by itself, a functionally effective derivative or as a fragment. Each class of substance has amine groups which can form salts in accordance with the invention. Amylin per se has four amino groups which therefore forms in the known production methods the tetratrifluoroacetic acid. It is believed that all the fragments which have amylin type activity, e.g. as set forth in European Patent 289287, will all have at least one amino group which will be capable of forming a salt. Where two or more amino groups are present in the substance, the possibility of mixed salts exists which are also within the scope of the invention.

However, the invention requires that all the trifluoroacetic acid or other bone inhibitory acetic acid anions be removed or alternatively be present in such minor amounts as to have no therapeutic effect.

The compounds of the invention can be formulated into pharmaceutical compositions in the normal way to make oral, intranasal or parenteral formulations dependent upon the desired form of administration of the substance.

The amylin or amylin agonist is administered in an amount to meet the particular condition under treatment. It will be administered to the mammal either injectably, intranasally or in an oral formulation in a form for ensuring the availability of the amylin agent at the particular site for effective therapy. Amylin like most long chain peptides is generally inactive when taken orally. Fragments of amylin have been reported to have amylin like activity for other indications and it is anticipated that a fragment of amylin may have bone stimulation effects. Fragments which are small peptides may be able to be effective orally. Parenteral administration is therefore expected to be the most commonly employed either subcutaneously or intramuscularly. For the treatment of fractures or other localised bone disorders, application of amylin directly to the site is desirable e.g. by injection or by application during surgery. It is believed that the dosage administered will lie within the range 0.01–100 mg/kg of body weight. The actual dose administered to each patient will depend on the type of patient and the nature of the disorder being treated. It is envisaged that for prophylactic therapy the dose will be lower than that required for reversal of bone resorption or treatment of fractures.

Administration of two or more compounds selected from amylin or amylin agonists is within the scope of the invention as is the use of an amylin compound with any other effective therapeutic agent (e.g., insulin) including any other agent for treatment of bone disorders. Combination agent therapy can be by separate administration of the individual agents or by combining the two or more agents into one composition form.

BEST MODE OF CARRYING OUT THE INVENTION

The invention will now be described by way of Example with reference to the attached drawings in which:

FIG. 1 Dose-dependence of the effects of rat amylin and rat calcitonin gene-related peptide-1 (CGRP) and rat calcitonin on numbers of osteoblast-like cells in culture over 24 hours. Cells were either (a) growth-arrested as a result of being cultured in the presence of 0.1% bovine serum albumin or (b) were actively growing in culture medium containing 2% fetal calf serum. n=6 in each group. Data are mean ± sem. Statistical significance (by Student's test) of differences from control: $*p \leq 0.05$; $p<0.005$; $*p<0.001$.

When osteoblast-like cells were exposed to $4\times10^{-8}$M TFA for 24 hrs cell numbers declined from $5.6\pm0.3\times10^4$ in control cultures to $4.2\pm0.3\times10^4$ (p=0.006).

Furthermore the following table shows clearly the beneficial effect of removing the TFA anion.

| Osteoblast numbers after 24 h culture | | | |
|---|---|---|---|
| Treatment | Osteoblast Numbers | n (wells) | P (v s control) |
| Control | 4.6 ± 0.64 | 6 | |
| Amylin, TFA Salt, $10^{-8}$M | 5.6 ± 0.96 | 6 | 0.06 |
| Amylin, chloride salt, $10^{-8}$M | 7.9 ± 1.00 | 5 | <0.001 |

(Data are mean ± SD, $10^4$ cells/well).

The chloride salt is prepared as follows:
Dissolve 10μ moles of peptide in 50 μl of 3 mM hydrochloric, acid.
Leave at room temperature for 1 hour.
Dry down in freeze-drier.
Redissolve in 50 μl of pure water with sonication.

Figure 2:
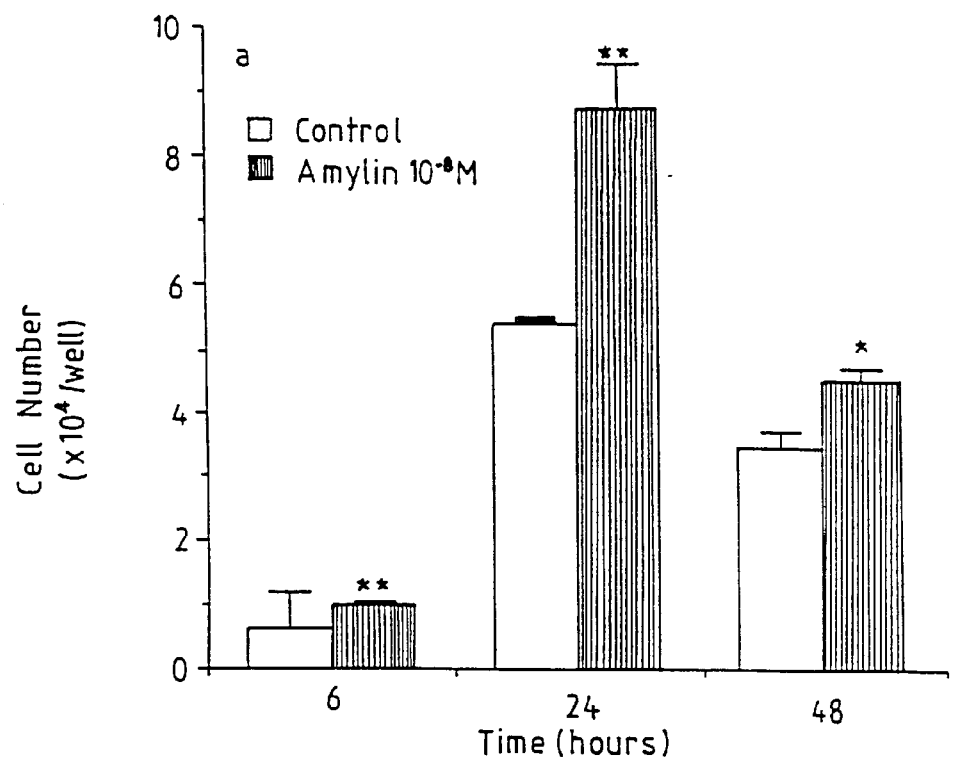

FIG. 2 Time-course of the effect of rat amylin on proliferation of osteoblast-like cells from fetal rat calvariae. Statistical significance of differences from control at each time-point: *p≦0.02; **p<0.005.

Figure 3:
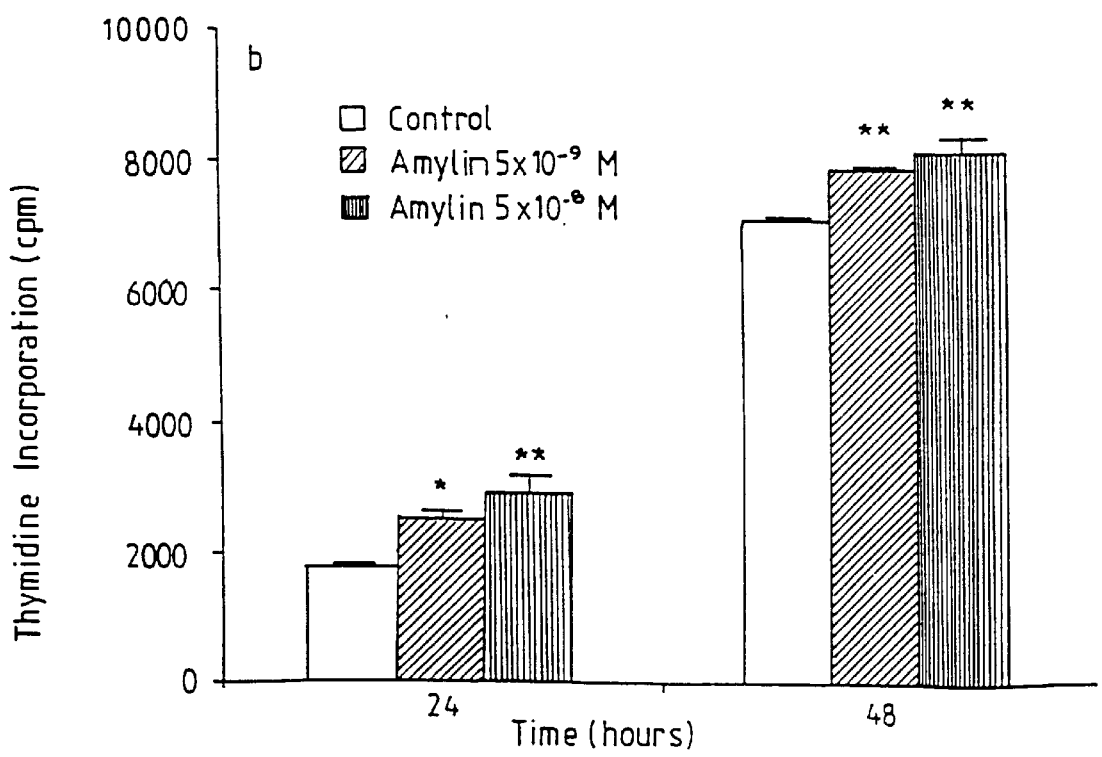
Figure 4A:
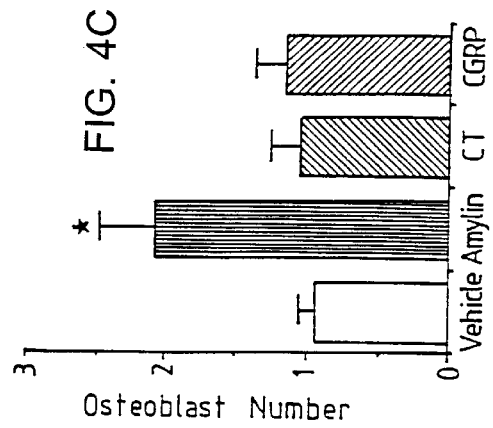
Figure 4B:
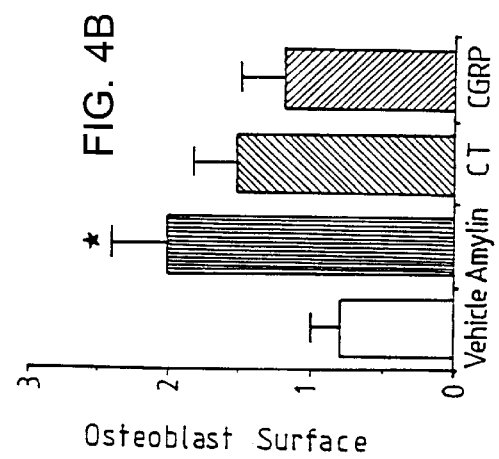
Figure 4C:
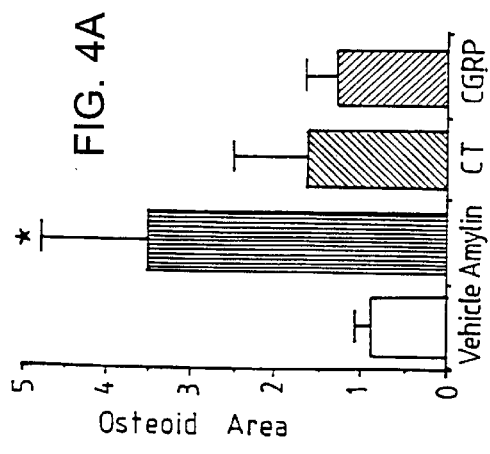
Figure 4D:
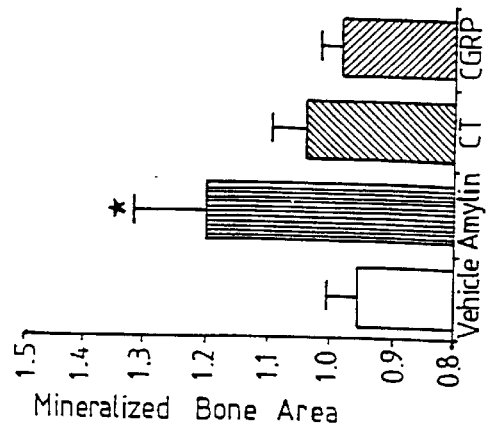
Figure 4E:
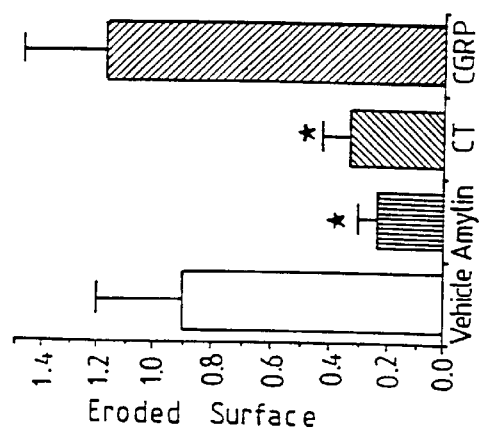
Figure 4F:
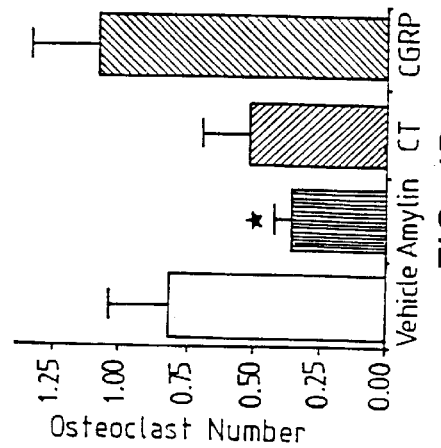

FIG. 3 The effect of rat amylin on thymidine incorporation into osteoblast-like cells from fetal rat calvariae. Statistical significance of differences from control at each time-point: *p=0.002; **p<0.001. In both experiments the culture medium contained 0.1% bovine serum albumin. n=6 in each group. Data are mean ± sem.

FIG. 4 Comparison of the in vivo effects of rat amylin, rat calcitonin (CT) and rat CGRP in adult mice. The daily dose of each peptide was $4.1 \times 10^{-9}$ mol. Data are expressed as the ratio of each index measured in the injected hemicalvaria to that measured in the contralateral, uninjected hemicalvaria. n=5 in each group. Data are mean ± sem. Significant differences (p<0.05) between the injected and uninjected hemicalvariae are indicated by asterisks.

METHODS

Osteoblast-like cells were prepared by sequential collagenase digestion of calvariae from 20 day fetal rats, as described previously, Lowe, C., Cornish, J., Callon, K, Martin, T. J., and Reid, I. R. (1991) J. Bone Miner. Res. 6, 1277–1283. The osteoblastic phenotype of these cells has been established by the demonstration of high levels of alkaline phosphatase and ostcalcalcin, and a sensitive adenylate cyclase response to parathyroid hormone and prostaglandins.

The effects of the peptides on bone histology in vivo were assessed by subcutaneously injecting the peptide daily for 5 days over the periosteum of the right hemicalvaria of adult, male Swiss-Webster mice. The animals were sacrificed 1 week following the last injection. Non-decalcified sections of the calvariae were prepared as described previously, Cornish, J., Callon, K., King, A., Edgar, S., and Reid, I. R. (1993) Endocrinology 132, 1359–1366. Quantitative histomorphometry was performed by an operator blinded to the treatment each animal had received. Data are expressed as the ratio of each index measured in the injected hemicalvaria to that measured in the contralateral, uninjected hemicalvaria of the same animal and have been evaluated by paired t tests.

RESULTS

Osteoblast Studies

Exposure of growth-arrested cultures of fetal rats osteoblast-like cells to amylin for 24 hours resulted in a substantial, dose-related increase in cell number (FIG. 1a).

The related peptide, calcitonin gene-related peptide (CGRP), also increased osteoblast proliferation, but the effect was smaller and only significant at $10^{-8}$M. Rat calcitonin ($10^{-9}$–$10^{-7}$M) and salmon calcitonin ($10^{-7}$M) were without effect, and parathyroid hormone ($10^{-8}$M) reduced cell numbers 18% at 24 hours (p=0.025) (data not shown). Amylin's stimulation of osteoblast proliferation was not dependent on the basal growth rate of the cells and was also observed in actively growing cells (FIG. 1b). The effect of amylin on osteoblast proliferation was sustained over time, as judged both by cell number which was increased in amylin-treated cells from 6 to 48 hours (FIG. 2), and by a sustained increase in DNA synthesis assessed by thymidine incorporation (FIG. 3).

In Vivo Calvarial Studies

The effects of amylin on bone in vivo were compared with those of equimolar amounts of calcitonin and CGRP by injecting the peptides daily over the calvariae of live adult mice. Vehicle injection had no effect on any histomorphometric index (FIG. 4). In contrast, amylin produced two- to three-fold increases in the indices of bone formation and decreases in bone resorption of comparable magnitude. Mineralized bone area did not significantly change indices of bone formation but calcitonin reduced eroded surface to a similar extent to amylin. However, mineralized bone area was increased only 4% by calcitonin, a non-significant effect. The bone was histologically normal in all the treatment groups—there was no evidence of woven bone formation. Weight gain did not differ between treatment groups and the animals remained healthy, as judged by coat condition and behaviour.

Following the method used under FIG. 1 when osteoblast-like cells were exposed to human and rat amylin $10^{-9}$M results were as follows:

| Osteoblast numbers after 24 h culture | | | |
|---|---|---|---|
| Treatment | Osteoblast Numbers | n | p (vs control) |
| Control | 4.2 ± 0.6 | 6 | |
| rat amylin $10^{-9}$M | 5.9 ± 0.8 | 6 | 0.003 |
| human amylin $10^{-9}$M | 6.1 ± 0.9 | 6 | 0.003 |

(Data are mean ± SD, $x10^4$ cells/well).

We have also conducted the following systemic in vivo experiment where amylin at a concentration of $10^{-8}$M is injected subcutaneously.

Calvarial Histomorphometry
11 mice in each treatment group.
Differences between control and amylin groups were statistically tested using an unpaired Student t test.
Measurements are recorded per mm calvarial length.

| Parameters | Treatment | mean | sem | p |
|---|---|---|---|---|
| Bone Formation Indices | | | | |
| osteoid area (mm²) | control | 0.0005 | 0.0001 | 0.001 |
| | amylin | 0.0018 | 0.0003 | |
| osteoblast surface (mm) | control | 0.85 | 0.12 | 0.026 |
| | amylin | 1.76 | 0.06 | |
| osteoblast number | control | 73.6 | 9.0 | <0.0001 |
| | amylin | 147.5 | 8.8 | |

-continued

| Parameters | Treatment | mean | sem | p |
|---|---|---|---|---|
| Bone Resorption Indices | | | | |
| eroded surface (mm) | control | 0.294 | 0.036 | 0.002 |
| | amylin | 0.081 | 0.013 | |
| osteoclast surface (mm) | control | 0.094 | 0.016 | <0.0001 |
| | amylin | 0.019 | 0.002 | |
| osteoclast number | control | 3.6 | 0.3 | 0.002 |
| | amylin | 1.2 | 0.1 | |

In the above systemic test, amylin has produced significant increases in all indices of bone formation and significant decreases in indices of bone resorption compared to control. These results are in agreement with the results showing the effects of amylin on bone in vivo, when the peptide is injected locally.

These results establish amylin as a stimulator of osteoblast proliferation. In vitro, the effect of amylin on osteoblast numbers is similar to or greater than that of the established osteblast growth factors, transforming growth factor-β, epidermal growth factor, and insulin-like growth factors 1 and 2, studied in comparable systems Herrmann-Erlee, M. P. M. and van der Meer, J. M. (1990) Calcif. Tissue Int. 46, A21; Ng, K. W., Partridge, N. C., Niall, M., and Martin, T. J. (1983) Calcif. Tissue Int. 35, 624–628.; Guenther, H. L., Cecchini, M. G., Elford, P. R., and Fleisch, H. (1988) J. Bone Miner. Res. 3, 269–278.; Wrana, J. L., Maeno, M., Hawrylshyn, B., Yao, K., Domenicucci, C., and Sodek, J. (1988) J. Cell. Biol. 106, 915–924.; McCarthy, T. L., Centrella, M., and Canalis, E. (1989) Endocrinology 124, 301–39. The present data demonstrate stimulation of osteoblast proliferation at amylin concentrations comparable to those found in the circulation of normal subjects, Butler, P. C., Chou, J., Carter, W. B., Wang, Y. -N., Bu, B. -H., Chang, D., Chang, J. -W., and Rizza, R. A. (1990) Diabetes 39, 752–756.; Sanke, T., Hanabusa, T., Nakano, Y., Oki, C., Okai, K., Nishimura, S., Kondo, M., and Nanjo, K. (1991) Diabetologia 34, 129–132; Mitsukawa, T., Takemura, J., Asai, J., Nakazato, M., Kangawa, K., Matsuo, H., and Matsukura, S. (1990) Diabetes 39, 639–642, even without making allowance for the high rates of loss of amylin onto the surfaces of laboratory plasticware, Young, A. A., Gedulin, B., Wolfelopez, D., Greene, H. E., Rink, T. J., and Cooper, G. J. S. (1992) Am. J. Physiol. 263, E274–E281. This suggests that amylin may be a physiological regulator of osteoblast function. There is some evidence for amylin production by osteoblasts, Gilbey, S. G., Ghatei, M. A., Bretherton-Watt, D., Zaidi, M., Jones, P. M., Perera, T., Beacham, J., Girgis, S., and Bloom, S. R. (1991) Clin. Sci. 81, 803–808, so its concentration in the bone microenvironment may be considerably higher than that found to be minimally active in these studies.

The in vivo model used in these studies is relatively new but has been used to assess the effects of a variety of hormones and cytokines on bone, Cornish, J., Callon, K., King, A., Edgar, S., and Reid, I. R. (1993) Endocrinology 132, 1359–1366; Boyce, B. F., Aufdemorte, T. B., Garrett, I. R., Yates, A. J. P., and Mundy, G. R. (1989) Endocrinology 125, 1142–1150; Garrett, i. R., Boyce, B. F., Oreffo, R. O., Bonewald, L., Poser, J., and Mundy, G. R. (1990) J. Clin. Invest. 85, 632–639; Mackie, E. J. and Treschel, U. (1990) Bone 11, 295–300; Tanaka, T., Taniguchi, Y., Gotoh, K., Satoh, R., Inazu, M., and Ozawa, H. (1993) Bone 14, 117–123. In general, the findings in this model have been consistent with those from other systems and are in accord with current understanding of the action of this wide range of factors in human bone physiology.

Postmenopausal osteoporosis is an increasing health problem as a result of the aging of the population. Despite recent therapeutic advances there is a need for safer and more effective therapies. Most currently available treatments primarily inhibit bone resorption and are, therefore, limited in the extent to which they can reverse pre-existing bone loss. The discovery of a compound which combines anti-resorptive properties with stimulation of bone formation, and thus results in substantially greater increases in bone mass than are produced by calcitonin, offers the possibility of a novel therapy for this chronic disabling condition.

Industrial Applicability

The invention will find wide applicability in the treatment of bone disorders such as osteoporosis, arthritides. Amylin can be used to increase or maintain bone density in a subject. The invention will therefore be of enormous benefit in the treatment of subjects and in the provision of agents and use of them to treat subjects.

We claim:

1. Amylin or amylin agonist in a form free of trifluoroacetic acid.

2. Amylin or an amylin agonist in the form of a hydrochloride salt.

3. A pharmaceutical composition comprising amylin or an amylin agonist in a form free of trifluoroacetic acid together with a suitable carrier.

4. A method of stimulating bone growth comprising subjecting to the effect of an effective amount of amylin or an amylin agonist in a form free of trifluroacetic acid.

5. The method of claim 4 in which the amylin or amylin agonist is in the form of a salt.

6. A method of treatment of fractures of bone comprising administering to the fracture site an effective amount of amylin or an amylin agonist in a form free of trifluoroacetic acid.

7. The method of claim 6 in which the amylin or amylin agonist is in the form of a salt.

8. A method of prophylactically increasing or maintaining bone density in a subject having a substantially normal bone density comprising the step of administering an amount of amylin or an amylin agonist to said subject effective to stimulate osteoblast proliferation.

9. The method of claim 8 in which the amylin or amylin agonist is in the form of a salt.

10. A method of stimulating bone growth through increasing osteoblast proliferation comprising subjecting the bone to the effect of an effective amount of amylin or an amylin agonist in a form free of trifluroacetic acid.

11. A method of improving the effectiveness of amylin or an amylin agonist in improving or maintaining bone density comprising the step of making amylin in a form free of trifluroacetic acid.

* * * * *